US00PP18213P2

(12) United States Plant Patent
Kaagman

(10) Patent No.: US PP18,213 P2
(45) Date of Patent: Nov. 13, 2007

(54) ***CAMPANULA* PLANT NAMED 'CAMP WHIT'**

(50) Latin Name: *Campanula isophylla Moretti*
Varietal Denomination: Camp Whit

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/412,517
(22) Filed: Apr. 27, 2006
(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOVROM Citation For 'Camp Whit' as per QZ PBR 20050115; filed Jan. 24, 2005.*

* cited by examiner

*Primary Examiner*—Kent Bell
(74) *Attorney, Agent, or Firm*—Jondle & Associates, P.C.

(57) ABSTRACT

A new *campanula* plant particularly distinguished by large, wide open, white, star-shaped flowers, an early and floriferous flowering response, grass-green foliage with cordate leaves, medium vigorous growth, good-branching ability, compact, rounded mounding and even plant habit, is disclosed.

2 Drawing Sheets

Genus and species: *Campanula isophylla* Moretti.
Variety denomination: 'Camp Whit'.

BACKGROUND OF THE NEW PLANT

The present invention comprises a new and distinct cultivar of *campanula,* botanically known as *Campanula isophylla* Moretti, and hereinafter referred to by the cultivar name 'Camp Whit'. The new cultivar originated from a hybridization made in February 2000 in Andijk, The Netherlands. The female parent was 'CW-128-1', a proprietary (unpatented) white-flowered *Campanula isophylla* plant, while the male parent was 'CR-2-1', a proprietary (unpatented) white-flowered *Campanula isophylla* plant. The seeds produced by the hybridization were sown in August 2000, and the resulting seedlings were selected in January 2002. A single plant selection was chosen for further evaluation and for asexual propagation in 2002.

The new cultivar was created in 2000 in Andijk, The Netherlands and has been asexually reproduced repeatedly by vegetative cuttings and tissue culture in Andijk, The Netherlands over a five-year period. 'Camp Whit' has also been trialed at Gilroy, Calif. and Hillscheid, Germany. The present invention has been found to retain its distinctive characteristics through successive asexual propagations.

Plant Breeder's Rights for this cultivar were applied for in Canada on Mar. 21, 2006 and with the European Union on Jan. 24, 2005.

SUMMARY OF THE INVENTION

The following are the most outstanding and distinguishing characteristics of this new cultivar when grown under normal horticultural practices in Andijk, The Netherlands and Hillscheid, Germany.

1. Large, wide-open, white, star-shaped flowers;
2. An early and floriferous flowering response;
3. Green-grass foliage with cordate leaves;

4. Good branching ability;
5. Medium vigorous growth; and
6. A compact, rounded, even and mounding plant habit.

DESCRIPTION OF PHOTOGRAPHS

This new *campanula* plant is illustrated by the accompanying photographs which show overall plant habit including blooms, buds, and foliage of the plant; the colors shown are as true as can be reasonably obtained by conventional photographic procedures. The photographs are of 7-month-old plants grown in a greenhouse in Andijk, The Netherlands in July 2004.

DESCRIPTION OF THE NEW CULTIVAR

Figure 1:
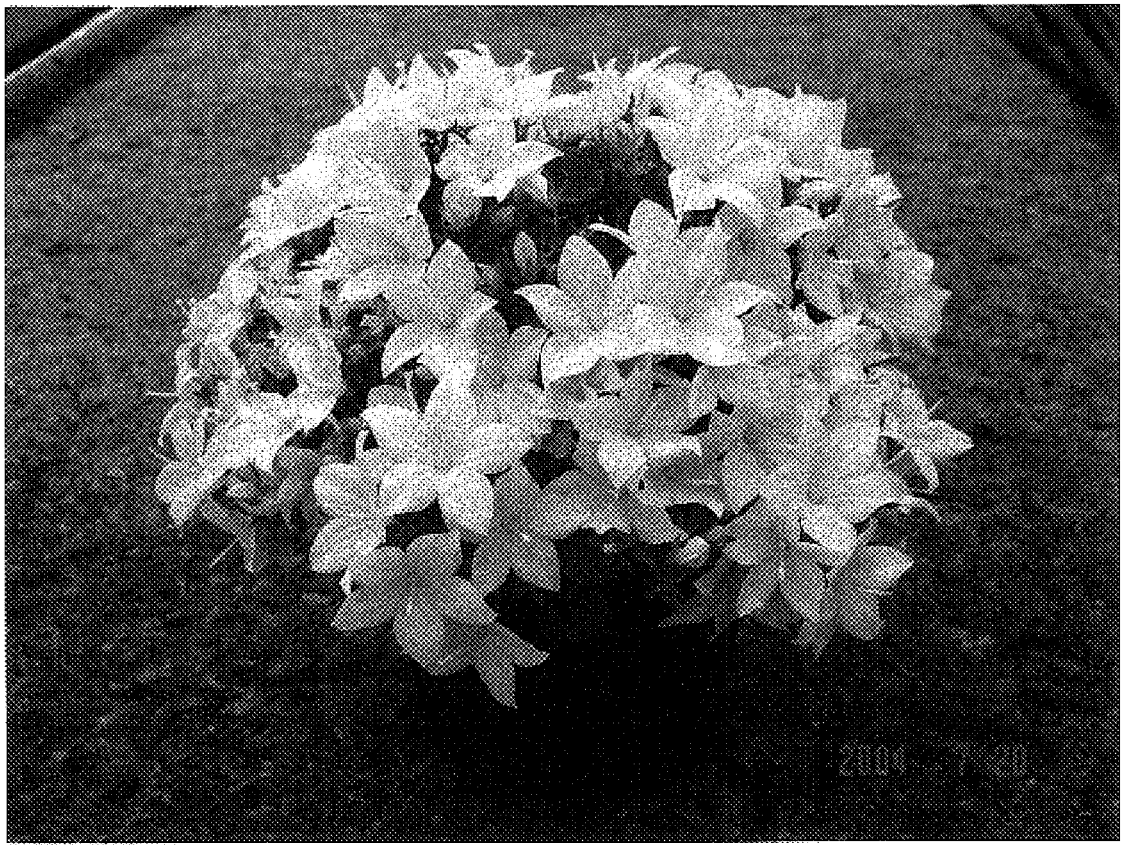
FIG. 1 shows the overall plant habit, including blooms, buds, foliage and plant habit.
Figure 2:
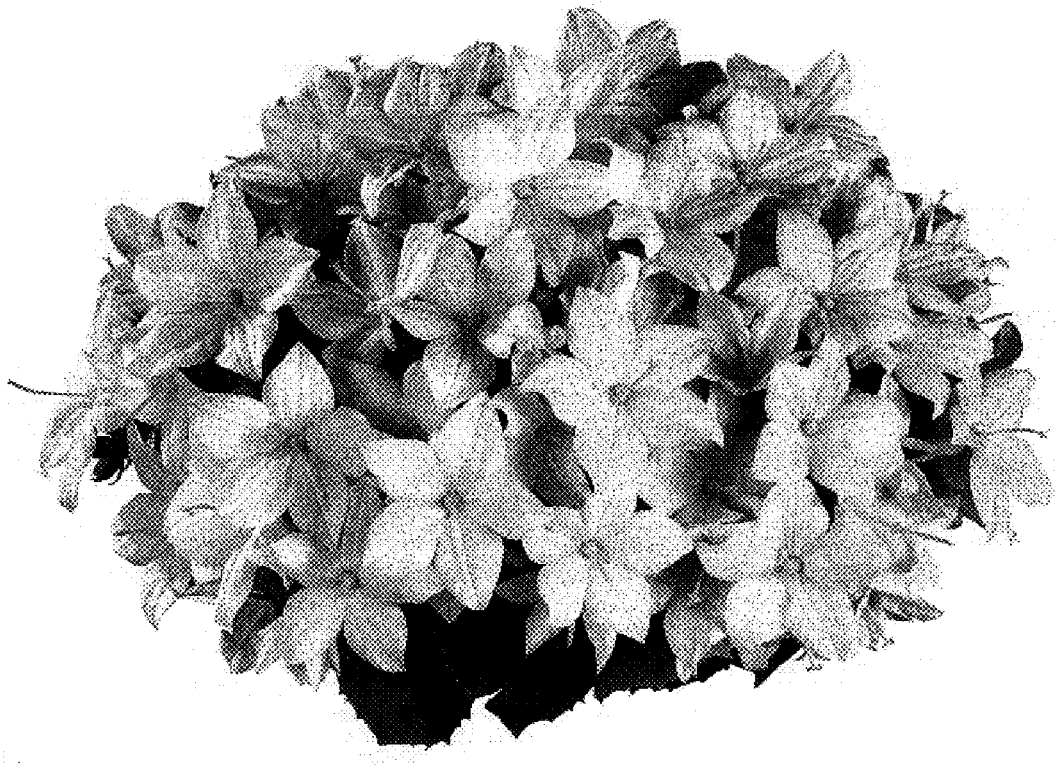
FIG. 2 shows a close-up of the mature inflorescences.

The following detailed description sets forth the distinctive characteristics of 'Camp Whit'. The data which define these characteristics were collected from asexual reproductions carried out in Andijk, The Netherlands. The plant history was taken partly on 5-week old plants, still in a vegetative state and grown in Hillscheid, Germany in the spring of 2006. Rooted cuttings were planted in 10.5-cm pots and grown in a greenhouse. The plants were not pinched. Flower observations were made on 35-week-old plants in fall of 2005. Color readings were taken under natural light. Color references are primarily to The R.H.S. Colour Chart of The Royal Horticultural Society of London (R.H.S.) (2001).

DETAILED BOTANICAL DESCRIPTION

Classification:
*Family.*—Campanulaceae.
*Botanical.*—*Campanula isophylla* Moretti.
*Common name.*—Italian Bellflower.

Parentage:

*Female parent.*—'CW-128-1', a proprietary (unpatented) white-flowered *Campanula isophylla* plant.

*Male parent.*—'CR-2-1', a proprietary (unpatented) white-flowered *Campanula isophylla* plant.

Growth:

*Form.*—Herbaceous perennial; for commercial purposes the variety can be cultivated as an annual.

*Habit.*—Relatively compact, well-branching, rounded plant habit; pinching results in a more even plant habit.

*Height (measured from the top of the soil).*—11 cm.

*Width (horizontal plant diameter).*—15 cm to 17 cm.

*Propagation.*—Terminal tips for cutting.

*Time to produce a finished flowering plant.*—11 to 13 weeks for a 10 cm to 12 cm pot.

*Outdoor plant performance.*—As flowering pot plants.

*Time to initiate and develop roots.*—25 days.

*Root description.*—Fibrous, fine and cream-white.

Stems:

*Average number of basal branches.*—9 to 11.

*Length.*—9 cm to 12 cm.

*Diameter (at midpoint).*—0.3 cm to 0.4 cm.

*Internode length.*—1.0 cm to 1.5 cm.

*Color.*—RHS 145A to RHS 145B (light-green).

*Anthocyanin.*—None.

*Texture.*—Covered with very short pubescence.

Leaves:

*Arrangement.*—Alternate, simple.

*Size.*—Length: 3.1 cm to 3.5 cm. Width: 3.8 cm to 4.2 cm.

*Shape.*—Cordate to round.

*Margin.*—Slightly serrate or denticulate.

*Apex.*—Rounded.

*Base.*—Cordate.

*Color.*—Immature leaves: Upper surface: RHS 143B. Lower surface: RHS 138B. Mature leaves: General: Medium green to grass-green. Upper surface: RHS 137D to RHS 143B. Lower surface: RHS 138B.

*Texture.*—Dense, short hair along the margin and along the leaf veins of the lower surface, sparse fine hair on the leaf blade.

*Venation.*—Intermediate between palmate and pinnate.

*Venation color.*—Upper surface: RHS 144B. Lower surface: RHS 145A.

*Petioles.*—Length: Variable, up to 6.0 cm. Width: 0.2 cm. Color: RHS 143C. Texture: Slightly winged at the upper part, dense pubescence, fine, short hair.

Flower bud:

*Shape.*—Narrow and oval (elongated) with furrows.

*Size.*—Length: 1.2 cm. Diameter: 0.6 cm.

*Color at tight bud.*—RHS 150D (nearly-white).

Inflorescence:

*Blooming habit.*—Continuous under long-day conditions.

*Inflorescence type.*—Terminal, bending and decumbent.

*Number of flowers per inflorescence.*—About 5 to 8 flowers and buds.

*Lastingness of individual blooms on the plant.*—About 14 days.

*Fragrance.*—None.

*Length.*—3.5 cm to 5.0 cm.

*Diameter.*—3.5 cm to 4.5 cm.

*Peduncle.*—Length: 2.0 cm to 4.0 cm. Diameter: 0.2 cm to 0.25 cm. Color: RHS 143B to RHS 143C (green). Texture: Fine pubescence.

*Pedicels.*—Length: Up to 2.5 cm. Diameter: 0.15 cm to 0.2 cm. Color: RHS 143B. Anthocyanin: None. Texture: Fine pubescence.

Flowers:

*Flower type.*—Single, solitary, actinomorphic; campanulate.

*Corolla.*—Shape: Wide open, shallow cup-shape; composed of 5 petals, acute lobes, mainly fused and open outward. Size: Diameter: 3.8 cm. Depth: 0.7 cm. Color: General: White. Upper surface: Whiter than RHS 155D. Lower surface: RHS 155A.

*Petals.*—Shape: Roughly ovate. Size: Length: 1.4 cm. Width: 1.1 cm. Quantity: 5. Apex: Broadly acute. Base: Fused. Margin: Entire. Texture: Glabrous.

*Calyx.*—Composed of 5 sepals fused at the base.

*Sepals.*—Number: 5. Color (both surfaces): RHS 143A (green). Length: 1.2 cm. Width: 0.5 cm. Shape: Narrow ovate. Apex: Acute. Base: Fused. Margin: Entire. Texture: With pubescence, mostly along the edges and veins.

Reproductive organs:

*Stamens.*—Quantity: 5. Filament: Color: RHS 155D (white). Length: 0.2 cm. Diameter: 0.1 cm. Anther: Color: RHS 4C. Size: Length: 0.3 cm to 0.4 cm. Diameter: 0.1 cm. Pollen: Color: RHS 6D (pale-yellow). Amount: Moderate.

*Pistil.*—Quantity: 1. Length: 1.8 cm. Stigma: Color: RHS 150D (pale yellow-green, nearly white). Shape: 3-lobed with brush-like-arranged hair below the stigma. Style: Color: RHS 150D. Length: 1.4 cm.

*Ovary.*—Type: Intermediate. Shape: Oval. Length: 0.4 cm. Diameter: 0.3 cm. Color: RHS 143B.

Fruit and seed set: None observed.

Disease and insect resistance: None special observations made.

COMPARISON WITH PARENTAL AND COMMERCIAL CULTIVARS

'Camp Whit' differs from the female parent 'CW-128-1' (unpatented) in that 'Camp Whit' has smaller flowers and a more compact plant habit than 'CW-128-1'. Additionally, 'Camp Whit' has an earlier and more free flowering response than 'CW-128-1'.

'Camp Whit' differs from the male parent 'CR-2-1' (unpatented) in that 'Camp Whit' has larger flowers, more vigorous growth and a better plant habit than 'CR-2-1'.

'Camp Whit' differs from all known *Campanula isophylla* commercial varieties in that 'Camp Whit' has a more compact plant habit and earlier flowering response than all of the known *Campanula isophylla* commercial varieties.

I claim:

1. A new and distinct cultivar of *campanula* plant as shown and described herein.

* * * * *